United States Patent
Piriou et al.

[19]

[11] Patent Number: 6,018,242
[45] Date of Patent: Jan. 25, 2000

[54] EDDY CURRENT PROBE HAVING FOUR ACTIVE ELEMENTS ARRANGED IN A QUADRILATERAL

[75] Inventors: Marc Piriou, Vincennes; Jacky Slazak, Aunay/Auneau, both of France

[73] Assignee: Intercontrole, Rungis Cedex, France

[21] Appl. No.: 08/996,553

[22] Filed: Dec. 23, 1997

[51] Int. Cl.[7] .......................... G01R 33/12; G01N 27/72
[52] U.S. Cl. ........................ 324/242; 324/241; 324/243
[58] Field of Search .................................... 324/234, 236, 324/237, 238, 239, 240, 241, 242, 243, 227

[56] References Cited

U.S. PATENT DOCUMENTS 4,107,605   8/1978   Hudgell .................................... 324/238

*Primary Examiner*—Walter E. Snow
*Attorney, Agent, or Firm*—Pearne, Gordon, McCoy & Granger LLP

[57] ABSTRACT

An eddy current probe for the nondestructive testing of electrically conductive material parts comprises four identical active elements (10a, 10b, 10c, 10d), at lease in pairs, whose centers are arranged in accordance with a square or a quadrilateral, whose diagonals intersect at right angles and have an intersection point located in the center of one of them. The major axes (18a, 18b, 18c, 18d) of said elements are oriented perpendicular to the plane of the square or intersect at the same point on the normal to the center of the square. The active elements are generally windings. Preferably, opposite windings (10a, 10c and 10b, 10d) of the square are connected pairwise in series, so as to produce magnetic fields, which are summated according to the diagonals of the square and the two pairs are connected to one another according to a differential arrangement or circuit.

24 Claims, 4 Drawing Sheets

EDDY CURRENT PROBE HAVING FOUR ACTIVE ELEMENTS ARRANGED IN A QUADRILATERAL

DESCRIPTION

1. Technical Field

The invention relates to an eddy current probe for the nondestructive testing of parts having random shapes and made from an electrically conductive material.

Such a probe has numerous applications in various industrial fields, for the local detection of faults in new or used parts. As a non-limitative example, the eddy current probe according to the invention can be used for periodically testing the tubes of steam generators equipping nuclear power stations.

2. Prior Art

At present numerous eddy current probes exist. These probes differ from one another by the number of windings forming them, the shapes and dimensions of said windings and their electrical connection modes when several windings are used.

The shapes of the windings particularly depend on the type of probe which it is wished to produce (encircling probe, internal probe or flat probe). The number of windings and their possible electrical connections are dependent on the type of measurement performed (absolute or differential) and the number of functions which it is wished to have fulfilled by each winding (excitation only, measurement only or simultaneous excitation and measurement).

Generally, existing eddy current probes are designed for a specific use determining both the number, shape and layout of the windings, as well as their electrical connection mode.

DESCRIPTION OF THE INVENTION

The invention relates to a point or local eddy current probe, whose geometry enables it to function in different ways as a function of the adopted electrical connection mode, said geometry being such that a preferred operating mode enables it to be particularly insensitive to variations of the air gap separating the probe from the part to be tested, as a result of a particularly low noise level.

According to the invention, this result is obtained by means of an eddy current probe, characterized in that it comprises four adjacent active elements having substantially identical geometries and electromagnetic characteristics, having geometrical centres arranged according to a square located in a plane orientable substantially parallel to one face of a part to be tested and having major geometrical axes intersecting at a point located on a normal to said plane passing through the centre of the square or parallel to said normal.

By placing such a probe in the vicinity of the part to be tested and ensuring a relative displacement between the sensor and the part, a particularly air gap variation-insensitive, nondestructive testing is achieved. Thus, the probe can be used for testing planar parts or parts having a certain curvature, as well as tubular parts from the inside or outside.

In a preferred embodiment oL the invention, the active elements are windings.

According to a preferred electrical connection mode, the active elements, whose geometrical squares are located at opposite apices of the square are connected pairwise in series, so as to produce magnetic fields summated according to each diagonal of the square, when said pairs of active elements are traversed by an electric current. The pairs of active elements are then interconnected in accordance with a differential circuit or arrangement.

According to another electric connection mode, a first of the active elements is connected to an electric supply means in order to form a transmitter and the two active elements closest to said transmitter are connected to one another according to a differential circuit and connected to a measuring means in order to form a receiver. The fourth active element is then unused.

In this connection mode, multiplexing means are advantageously interposed between the active elements and the electric supply and measuring means, so that each of the active elements becomes transmitter in turn according to a cycle passing through the successive apices of the square formed by said active elements. During a relative displacement in translation between the probe and part, said layout makes it possible to perform a fictitious rotation of the probe on itself about the normal to the plane of the square passing through the centre of the latter.

According to yet another connection mode, two of the active elements are connected according to a differential circuit whereas the other two active elements are unused. The probe then functions in the manner of a conventional differential probe with two windings.

In this connection mode, multiplexing means can also be interposed between the active elements and the electric supply and measuring means, so that at least two pairs of active elements having different orientations are connected in turn, in accordance with differential circuits. During a relative displacement in translation between the probe and part, said layout once again makes it possible to simulate a rotation of the probe on itself to detect different orientation faults.

According to another connection mode, the active elements, whose geometrical centres are located at opposite apices of the square are pairwise connected in accordance with two differential circuits, so as to form two separate sensors sensitive to different orientation faults or errors.

In this electrical connection mode, multiplexing means are also advantageously interposed between the sensors and the electric supply and measuring means, so that the two sensors are put into use sequentially. A rotation of the probe on itself is once again simulated during the relative displacement in translation between the probe and the part.

The invention also relates to an eddy current probe, comprising four adjacent active elements having geometrical centres arranged in accordance with a quadrilateral, whose diagonals are perpendicular and have an intersection point in the centre of one of them, said quadrilateral being located in a plane orientable substantially parallel to one face of a part to be tested, the four active elements having major geometrical axes intersecting at a point located on a normal to said plane, or are parallel to said normal, the pairs of active elements whose centres are located on opposite apices of the quadrilateral having substantially identical electromagnetic nature, geometry and characteristics.

The best results are obtained when the quadrilateral formed by the centres of the active elements is a lozenge.

BRIEF DESCRIPTION OF THE DRAWINGS

The invention is described in greater detail hereinafter relative to non-limitative embodiments and with reference to the attached drawings, wherein show.

DETAILED DESCRIPTION OF PREFERRED EMBODIMENTS

Figure 1:
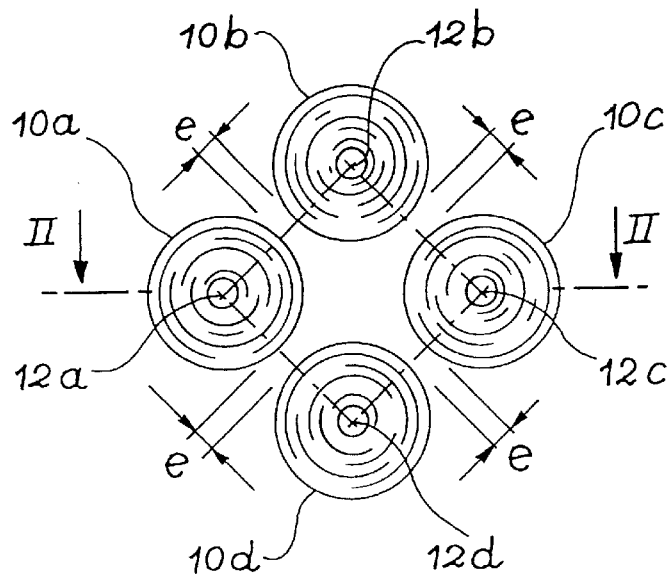
FIG. 1 A plan view solely showing the active elements of an eddy current probe according to the invention.
Figure 2:
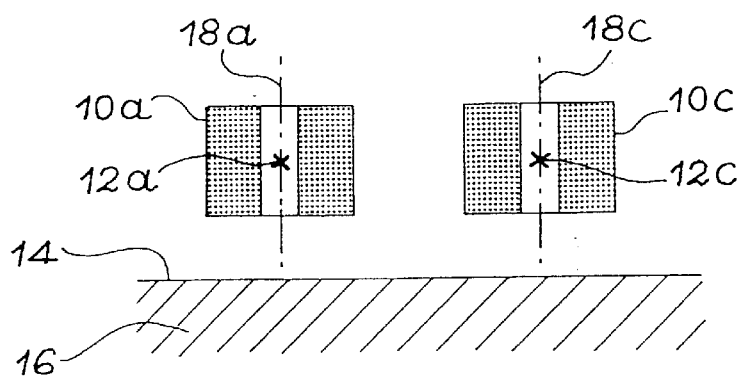
FIG. 2 A sectional view along line II—II in FIG. 1.

FIGS. 1 and 2 illustrate the geometrical layout of the active elements of a local or point eddy current probe according to the invention. This probe comprises four adjacent active elements, having substantially identical electromagnetic characteristics and geometries. Said active elements are respectively designated by the references 10a, 10b, 10c and 10d in FIG. 1. As shown in FIG. 1, the geometrical centres 12a, 12b, 12c and 12d of said active elements are arranged so as to form the consecutive apices of a square located in a plane oriented substantially parallel to one face 14 of a part 16 to be tested (FIG. 2).

In the embodiment illustrated in FIGS. 1 and 2, the major geometrical axes 18a, 18b, 18c and 18d of the active elements 10a, 10b, 10c and 10d are substantially parallel to one another and perpendicular to the plane of the square 12a, 12b, 12c, 12d.

Figure 3:
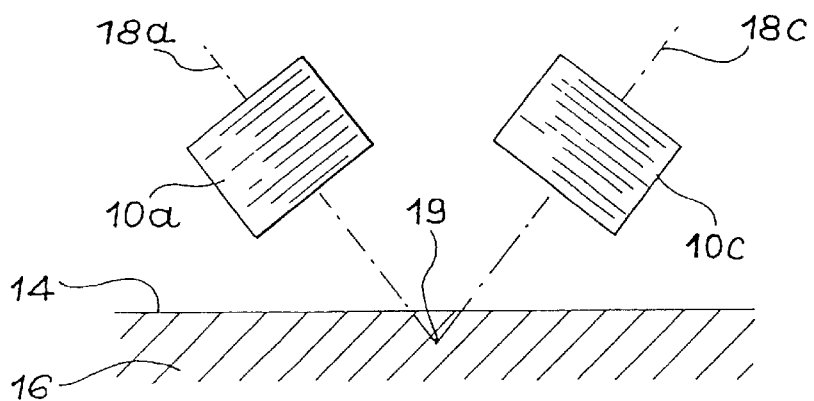
FIG. 3 A view comparable to FIG. 2 illustrating a variant.

In a variant diagrammatically illustrated in FIG. 3, said major axes 18a, 18b, 18c, and 18d all meet at the same point 19a located on the normal to the plane of the square 12a, 12b, 12c, 12d passing through the centre of said square.

The active elements 10a, 10b, 10c, 10d of the probe according to the invention are advantageously constituted by windings, which are generally cylindrical. They can also be formed by windings and ferrite cores associated with said windings.

The dimensions of said active elements can vary according to the envisaged application. In all cases, the distance e (FIG. 1) between adjacent active elements is very small compared with their diameter. For example, the distance e between the adjacent active elements which have a diameter of approximately 2 mm can be approximately 0.13 mm.

The four active elements of the probe are embedded in an electrically insulating support block (represented by a mixed line 21 in FIGS. 5 to 8). This support block is designed to be displaced relative to the part 16 to be tested, so as to carry out a scan of the complete surface 14 of said part. During said displacement, which can consist of a rectilinear translation or a more complex movement, the air gap separating the active elements 10a, 10b, 10c and 10d from the surface 14 of the part remains relatively constant. However, it can be subject to non-negligible variations in certain applications.

As will now be described with successive reference to FIGS. 4 to 8, the four active elements 10a, 10b, 10c and 10d can be connected in accordance with different modes adapted to different uses of the probe.

Figure 4:
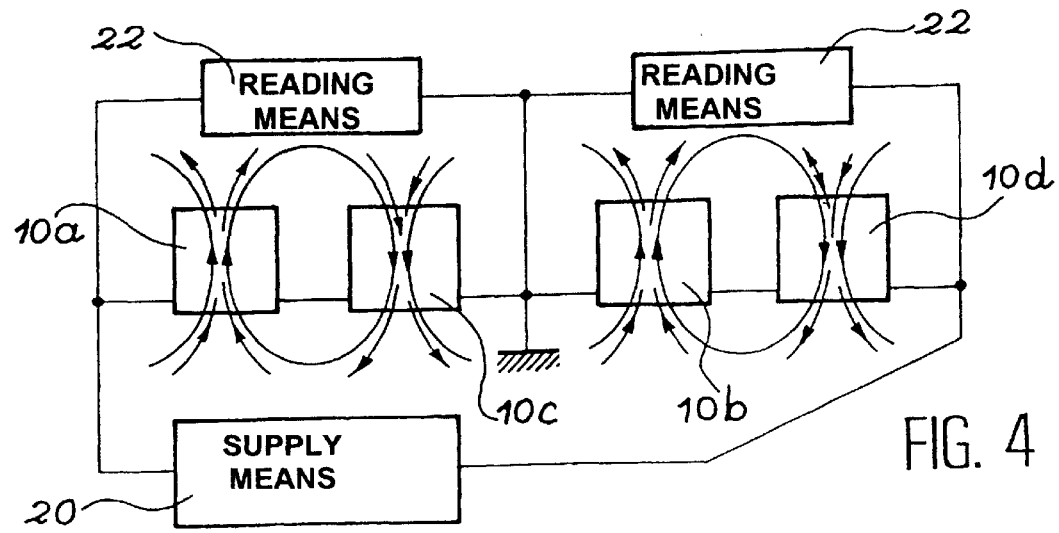
FIG. 4 A circuit diagram illustrating a first connection mode of the active elements of the probe according to the invention.

In a preferred connection mode illustrated in FIG. 4, the electrical connections are implemented so as to perform a differential measurement and such that each of the active elements acts both as the transmitter or excitation element or as the receiver or measuring element.

More specifically, in this preferred connection mode illustrated in FIG. 4, the active elements 10a and 10c on the one hand and the active elements 10b and 10d on the other, whose geometrical centres are located at opposite apices of the square, are pairwise connected in series. This connection is implemented in such a way that the electrical current supplying each of the two pairs of active elements 10a, 10c and 10b, 10d formed in this way produces magnetic fields summated according to each of the diagonals of the square and as is diagrammatically illustrated by the field lines in FIG. 4.

Moreover, the two pairs of active elements 10a, 10c and 10b, 10d are connected to one another according to a well-known, differential arrangement or circuit.

FIG. 4 also shows the supply means 20 supplying the excitation current of the active elements of the probe and the reading means 22 receiving and processing the signals at the terminals of each of the pairs of active elements 10a, 10c and 10b, 10d.

When the active elements of the probe are connected according to the first connection mode described with reference to FIG. 4, a relative displacement between the probe and the part, substantially parallel to the surface of the latter, permits a nondestructive testing of the part in a manner which is relatively insensitive to the value of the air gap. Thus, such a probe is particularly suitable for the testing of parts having an evolutive surface or when the relative displacement between the probe and the part does not make it possible to maintain a constant air gap throughout the measurement.

In the connection mode of FIG. 4, the probe according to the invention is substantially insensitive to the presence of faults oriented parallel to the sides of the square 12a, 12b, 12c, 12d. However, this disadvantage can be avoided by ensuring a displacement of the probe combining a translation and a rotation about an axis coinciding with the normal to the plane 12a, 12b, 12c, 12d passing through the centre of the square.

In a second connection mode for the active elements 10a, 10b, 10c and 10d of the probe, one of said active elements is used as the transmitter and the two active elements closest to said transmitter element are used as receivers. The fourth active element is then unused. For example, if the active element used as the transmitter is element 10a and the active elements used as receivers are elements 10b and 10d, the active element 10a is connected to the electric supply means 20 (FIG. 5) and the active elements 10b and 10d are connected in opposition to the measuring means 22, in accordance with a conventional differential circuit.

Figure 5:
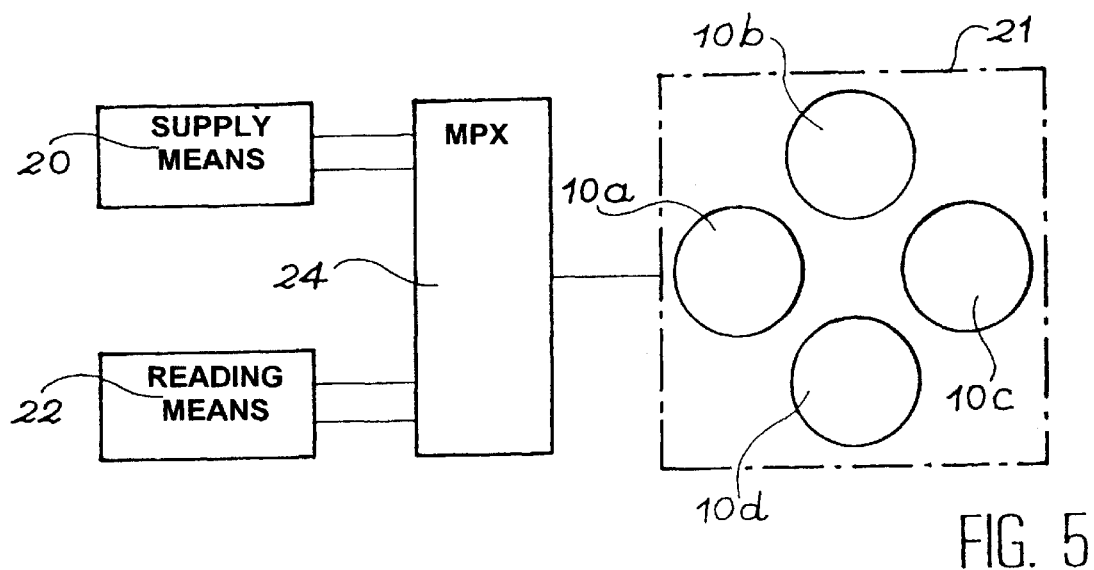
FIG. 5 A diagram showing a probe in which the excitation of the active elements and the measurement take place across multiplexing means.

As is diagrammatically illustrated in FIG. 5, advantageously multiplexing means 24 are interposed between the active elements 10a, 10b, 10c, 10d on the one hand and the electric supply 20 and measuring 22 means on the other. Thus, during the displacement in translation of the probe with respect to the part, this layout makes it possible to perform in fictional manner a circular scan by putting into operation the multiplexing means 24.

Figure 6:
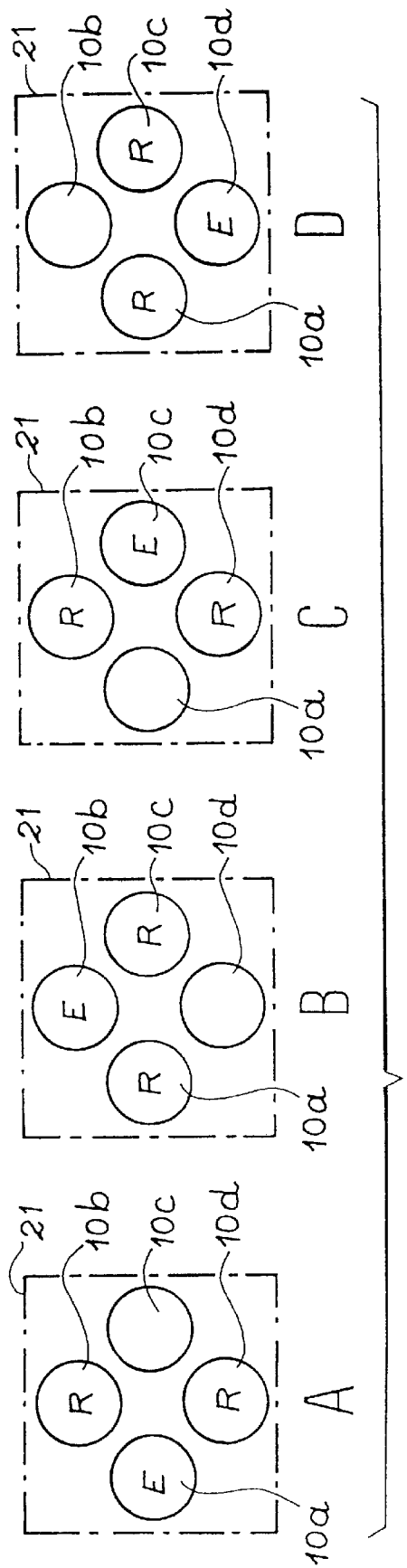
FIG. 6 Four successive stages of the operation of the probe according to FIG. 5, according to a second connection mode of said active elements.

As is diagrammatically illustrated in FIG. 6, the windings centred on adjacent apices of the square in turn become transmitters. They are designated by the letter E. The two windings adjacent to said transmitter winding E are on each occasion receivers and are designated by the letter R. Thus, FIG. 6 shows at A, B, C and D four successive states of the probe in which each of the active elements 10a, 10b, 10c and 10d in turn is the transmitter E, in accordance with a cycle passing through the successive apices of the square formed by said active elements. In said states A to D, the receiver active elements R are respectively the elements 10b and 10d, the elements 10c and 10a, the elements 10d and 10b and the elements 10a and 10c . On each occasion, the fourth active element, respectively 10c, 10d, 10a and 10b, remains unused.

Figure 7:
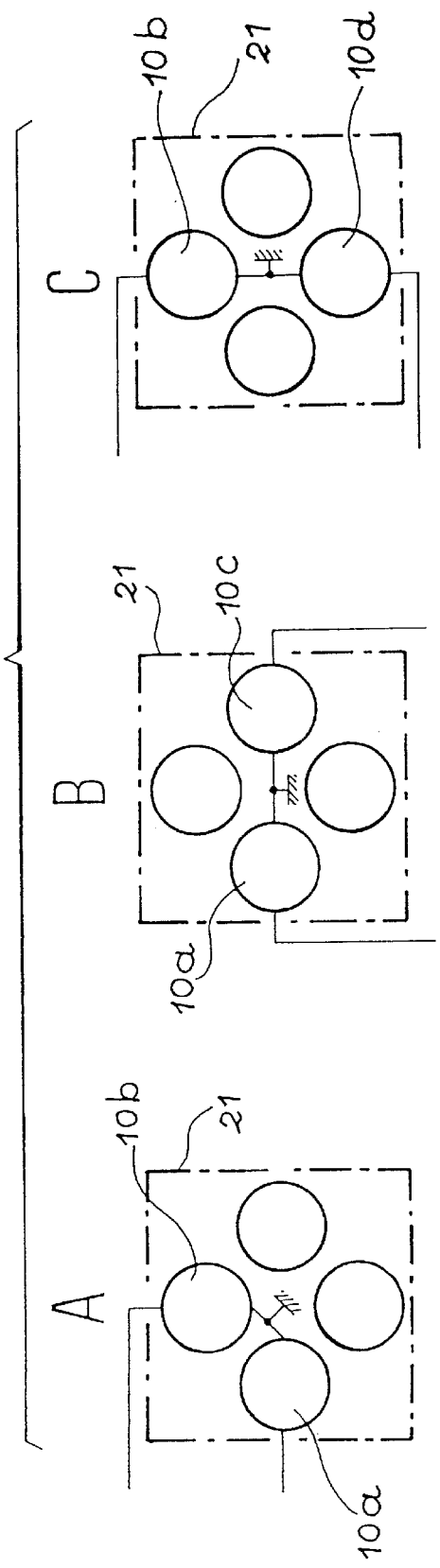
FIG. 7 Three successive stages in the operation of the probe according to FIG. 5 in a third connection mode of said active elements.

As is respectively illustrated at A, B and C in FIG. 7, in a third electrical connection mode of the active elements 10a, 10b, 10c and 10d of the probe, only a random two of these elements are electrically interconnected according co a differential circuit, the remaining two elements remaining unused. In this layout, the two electrically interconnected active elements form a conventional differential sensor with two windings, electrically connected both to the electric supply means and to the measuring means (not shown).

As a function of whether the active elements electrically connected are elements centred on adjacent apices of the square, such as elements 10a and 10b illustrated at A, or active elements centred on opposite apices, like elements 10a and 10c or 10b and 10d , as illustrated at B and C, the orientation of the thus formed sensor is not the same.

More specifically, it is possible to see at A, B and C in FIG. 7 that sensors formed by the connection of two adjacent active elements such as elements 10a and 10b or by the connection of two opposite active elements such as elements 10a and 10c or elements 10b and 10d have orientations at 90 or 45° with respect to one another By adopting a configuration identical to that illustrated in FIG. 5, i.e. by interposing multiplexing means 24 between the active elements on the one hand and the electric supply 20 and measuring 22 means on the other, it is possible to successively pass the probe into identical states to those illustrated at A, B and C in FIG. 7. This layout then makes it possible to ensure a fictitious rotation of the probe about an axis perpendicular to the plane 12a, 12b, 12c, 12d and passing through the centre of the square, during a displacement in translation of the probe with respect to the part.

Figure 8:
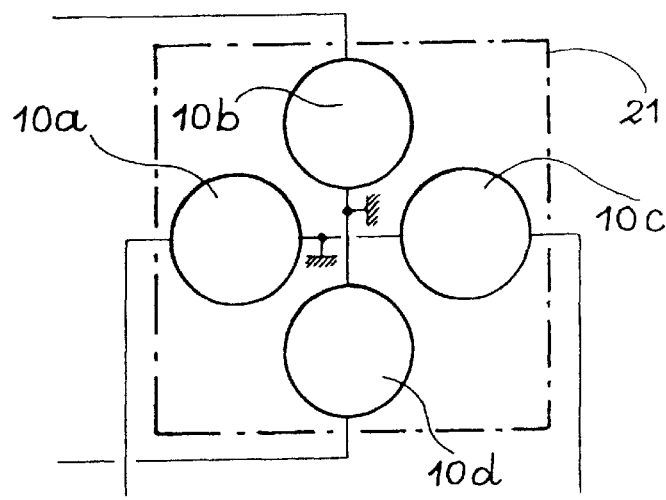
FIG. 8 A fourth connection mode of the active elements of the probe according to the invention.

Finally and as is diagrammatically illustrated in FIG. 8, in a further connection mode of the active elements of the probe, the active elements 10a and 10c on the one hand and 10b and 10d on the other, whose geometrical centres are located at opposite apices of the square, are pairwise connected according to two differential circuits or arrangements. Thus, within the same probe are formed two separate sensors oriented at 90° with respect to one another. According to the envisaged application, said two sensors 10a, 10c and 10b, 10d can be simultaneously or sequentially used. In the latter case, use is made of multiplexing means 24 interposed between the active elements on the one hand and the electric supply 20 and measuring 22 means on the other, as illustrated in FIG. 5.

The above description shows that the arrangement of the active elements of the probe according to the invention makes it possible to envisage different connection modes according to the envisaged application, whilst still having important intrinsic advantages when used in its preferred connection mode illustrated in FIG. 4.

The probe described in conjunction with FIGS. 1 and 2 comprises four identical active elements arranged in squares. However, the advantages specific to the probe according to the invention are not limited to this particular arrangement.

Figure 9:
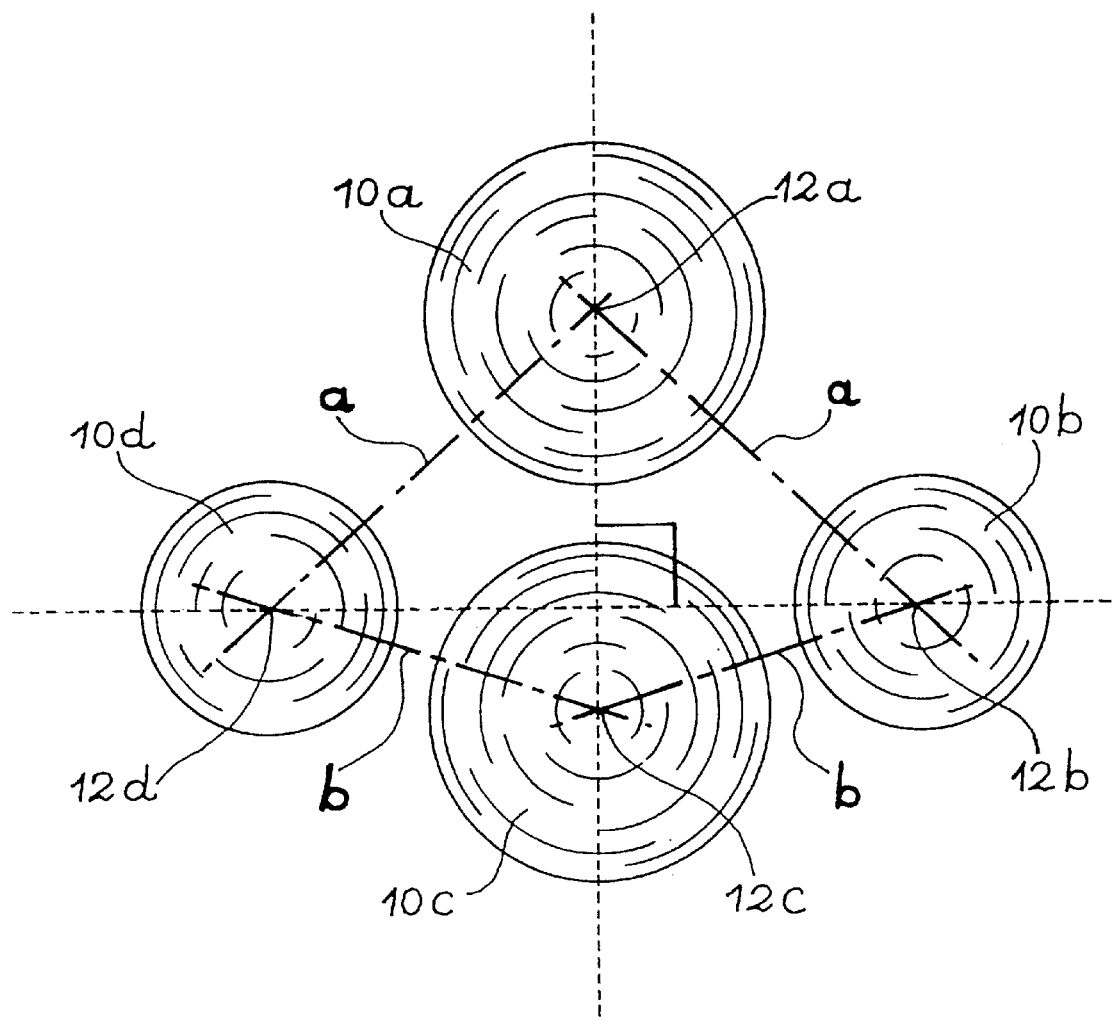
FIG. 9 Diagrammatically and in plan view another embodiment of the probe according to the invention.

Thus, as is very diagrammatically illustrated in FIG. 9, the quadrilateral formed by the geometrical centres 12a, 12b, 12c and 12d of the active elements 10a, 10b, 10c and 10d can be constituted by any quadrilateral, whose diagonals intersect at right angles and whereof at least one intersects the other in the centre in order to constitute the midperpendicular. In the case of FIG. 9, it is the diagonal joining the geometrical centres 12a, 12c, which intersects the other diagonal in its centre. The reverse arrangement is also obviously possible.

In the thus formed quadrilateral, adjacent sides are equal in pairs. Thus, in the example of FIG. 9, the sides joining the geometrical centres 12a, 12b and 12a, 12d have the same length a and the sides joining the geometrical centres 12b, 12c and 12c, 12d have the same length b.

The results are optimized and consequently better, when the lengths a and b approach equality, i.e. when the quadrilateral formed by the geometrical centres of the active elements tends towards a lozenge shape. The previously described square shape constitutes a special case of said optimized solution.

Moreover, the pairs of active elements 10a, 10c and 10b, 10d, whose geometrical centres are located on the opposite apices of the quadrilateral, are of the same nature and have a substantially identical geometry and electromagnetic Characteristics. However, the active elements of the probe can differ between the individual pairs, on the basis of their nature, their dimensions and/or their electromagnetic characteristics.

It should be noted that all the electrical connection modes described in conjunction with FIGS. 4 to 8 are applicable to the sensor described hereinbefore with reference to FIG. 9.

What is claimed is:

1. Eddy current probe having four adjacent active elements of substantially identical electromagnetic characteristics and geometries, having geometrical centers arranged according to a square located in a plane substantially orientable parallel to one face of a part to be tested and having major geometrical axes intersecting at one point located on a normal to said plane passing through the center of the square or parallel to said normal wherein a first of the active elements is connected to an electric supply means to form a transmitter, the two active elements closest to said transmitter are connected to one another in accordance with a differential circuit and connected to a measuring means to form a receiver and the fourth active element is unused.

2. Probe according to claim 1, wherein the active elements are windings.

3. Probe according to claim 1, wherein the active elements, whose geometrical centers are located at opposite apices of the square are pairwise connected in series, so as to produce magnetic fields summated according to each diagonal of the square, when said pairs of active elements are traversed by an electric current and wherein the pairs of active elements are connected to one another according to a differential circuit.

4. Probe according to claim 1, wherein multiplexing means are interposed between the active elements and the electric supply and measuring means, so that each of the active elements becomes the transmitter in turn in accordance with a cycle passing through the successive apices of the square formed by said active elements.

5. Eddy current probe having four adjacent active elements of substantially identical electromagnetic characteristics and geometries, having geometrical centers arranged according to a square located in a plane substantially orientable parallel to one face of a part to be tested and having major geometrical axes intersecting at one point located on a normal to said plane passing through the center of the square or parallel to said normal, wherein two of the active elements are electrically interconnected according to a differential circuit, the two other active elements being unused.

6. Probe according to claim 5, wherein multiplexing means are interposed between the active elements and electric supply and measuring means, so that at least two pairs of active elements having different orientations are connected in turn according to a differential circuit.

7. Eddy current probe having four adjacent active elements of substantially identical electromagnetic characteristics and geometries, having geometrical centers arranged according to a square located in a plane substantially orientable parallel to one face of a part to be tested and having major geometrical axes intersecting at one point located on a normal to said plane passing through the center of the square or parallel to said normal, wherein the active elements, whose geometrical centers are located at opposite apices of the square are connected pairwise according to two differential circuits, so as to form two separate sensors and multiplexing means are interposed between the active elements and electric supply and measuring means, so that the two sensors are sequentially implemented.

8. Eddy current probe, comprising four adjacent active elements having geometrical centers arranged in accordance with a quadrilateral, whose diagonals are perpendicular and have an intersection point in the center of one of them, said quadrilateral being located in a plane orientable substantially parallel to one face of a part to be tested, the four active elements having major geometrical axes intersecting at a point located on a normal to said plane, or are parallel to said normal, the pairs of active elements whose centres are located on opposite apices of the quadrilateral having substantially identical, electromagnetic nature, geometry and characteristics, wherein the quadrilateral is a lozenge.

9. Probe according to claim 8, wherein the active elements are windings.

10. Probe according to claim 8, wherein the active elements whose geometrical centres are located at opposite apices of the quadrilateral are connected in series in pairs, so as to produce magnetic fields which are summated along each diagonal of the quadrilateral, when said pairs of active elements are traversed by an electric current, and wherein the pairs of active elements are connected to one another in accordance with a differential circuit.

11. Eddy current probe, comprising four adjacent active elements having geometrical centers arranged in accordance with a quadrilateral, whose diagonals are perpendicular and have an intersection point in the center of one of them, said quadrilateral being located in a plane orientable substantially parallel to one face of a part to be tested, the four active elements having major geometrical axes intersecting at a point located on a normal to said plane, or are parallel to said normal, the pairs of active elements whose centres are located on opposite apices of the quadrilateral having substantially identical, electromagnetic nature, geometry and characteristics, wherein a first of the active elements is connected to an electric supply means to form a transmitter, the two active elements closest to said transmitter are interconnected in accordance with a differential circuit and are connected to a measuring means in order to form a receiver and the fourth active element is unused.

12. Probe according to claim 11, wherein the multiplexing means are interposed between the active elements and the electric supply and measuring means, so that each of the active elements becomes the transmitter in turn in accordance with a cycle passing through the successive apices of the quadrilateral formed by said active elements.

13. Eddy current probe, comprising four adjacent active elements having geometrical centers arranged in accordance with a quadrilateral, whose diagonals are perpendicular and have an intersection point in the center of one of them, said quadrilateral being located in a plane orientable substantially parallel to one face of a part to be tested, the four active elements having major geometrical axes intersecting at a point located on a normal to said plane, or are parallel to said normal, the pairs of active elements whose centres are located on opposite apices of the quadrilateral having substantially identical, electromagnetic nature, geometry and characteristics, wherein two of the active elements are electrically interconnected in accordance with a differential circuit, the two other active elements being unused.

14. Probe according to claim 13, wherein the multiplexing means are interposed between the active elements and the electric supply and measuring means, so that at least two pairs of active elements having different orientations are connected in turn, in accordance with a differential circuit.

15. Eddy current probe, comprising four adjacent active elements having geometrical centers arranged in accordance with a quadrilateral, whose diagonals are perpendicular and have an intersection point in the center of one of them, said quadrilateral being located in a plane orientable substantially parallel to one face of a part to be tested, the four active elements having major geometrical axes intersecting at a point located on a normal to said plane, or are parallel to said normal, the pairs of active elements whose centres are located on opposite apices of the quadrilateral having substantially identical, electromagnetic nature, geometry and characteristics, wherein the active elements whose geometrical centers are located at opposite apices of the quadrilateral are connected in pairs in accordance with two differential circuits, so as to form two separate sensors and multiplexing means are interposed between the active elements and electrical supply and measuring means, so that the two sensors are sequentially implemented.

16. Probe according to claim 4, wherein the active elements are windings.

17. Probe according to claim 5, wherein the active elements are windings.

18. Probe according to claim 6, wherein the active elements are windings.

19. Probe according to claim 7, wherein the active elements are windings.

20. Probe according to claim 11, wherein the active elements are windings.

21. Probe according to claim 12, wherein the active elements are windings.

22. Probe according to claim 13, wherein the active elements are windings.

23. Probe according to claim 14, wherein the active elements are windings.

24. Probe according to claim 15, wherein the active elements are windings.

* * * * *

UNITED STATES PATENT AND TRADEMARK OFFICE
CERTIFICATE OF CORRECTION

PATENT NO. : 6,018,242
DATED : January 25, 2000
INVENTOR(S) : Piriou et al.

It is certified that error appears in the above-indentified patent and that said Letters Patent is hereby corrected as shown below:

On the Title Page, please add the Foreign Application Priority Data --September 13, 1996 France 96 11207--.

On the Title Page, please add --Application is a Continuation-in-Part (CIP) of U.S. Appl. 08/923,564 Filed September 4, 1997--.

On the Title Page, Section [57], ABSTRACT, Line 3, delete "lease" and insert --least--.

Column 1, Line 62, delete "oL" and insert --of--.

Column 3, Line 1, delete "shoving" and insert --showing--.

Column 5, Line 19, delete "co" and insert --to--.

Column 6, Lines 30-31, delete "Characteristics" and insert --characteristics--.

Signed and Sealed this

Thirteenth Day of March, 2001

Attest:

NICHOLAS P. GODICI

Attesting Officer     Acting Director of the United States Patent and Trademark Office